United States Patent [19]

McAllister

[11] 4,270,556
[45] Jun. 2, 1981

[54] PROPHYLAXIS STRIP
[75] Inventor: Charles B. McAllister, Edina, Minn.
[73] Assignee: Twelve West, Inc., Long Lake, Minn.
[21] Appl. No.: 143,185
[22] Filed: Apr. 24, 1980
[51] Int. Cl.³ .............................................. A61C 15/00
[52] U.S. Cl. .................................................... 132/89
[58] Field of Search ............................. 132/89, 90, 93
[56] References Cited
U.S. PATENT DOCUMENTS
3,754,332  8/1973  Warren, Jr. ............................ 132/93
4,155,216  5/1979  Griset, Jr. ............................. 132/89
4,221,015  9/1980  Andersson ........................ 132/84 R Primary Examiner—G. E. McNeill
Attorney, Agent, or Firm—Schroeder, Siegfried, Ryan, Vidas, Steffey & Arrett

[57] ABSTRACT

A reusable strip of perforated stainless steel for use following prophylaxis to remove any remaining plaque, calculus, and stains from interproximal surfaces and contact areas of the teeth without abrading or damaging tooth enamel.

15 Claims, 5 Drawing Figures

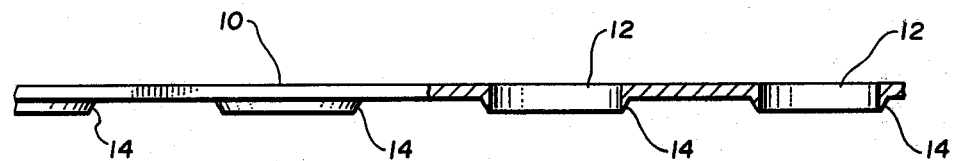
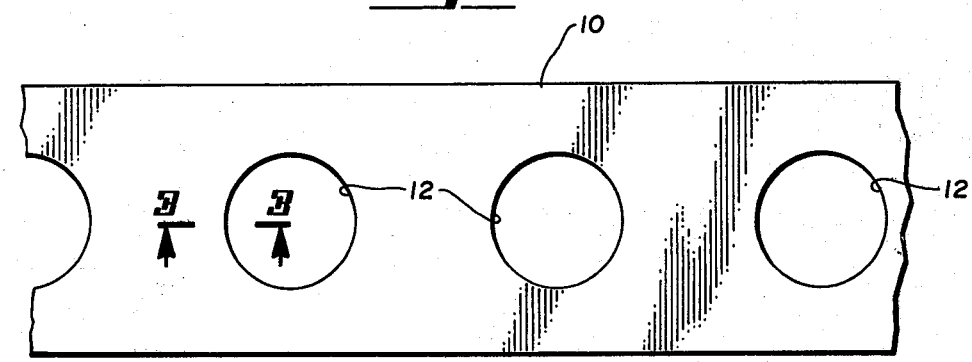
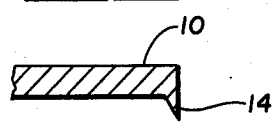
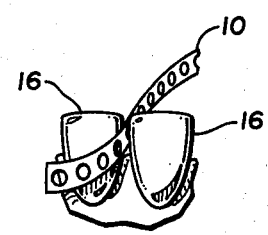
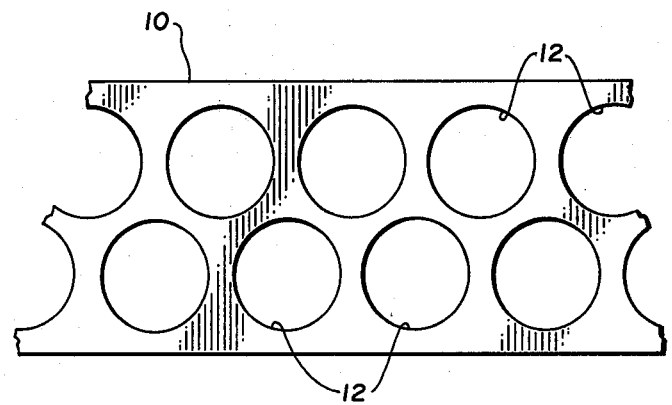

PROPHYLAXIS STRIP

DESCRIPTION

Background of Prior Art

This invention relates to a device for tooth cleaning. It is primarily directed to a device usable by professionals such as dentists and dental hygienists. However, it may be used by individuals.

The cleaning of human teeth generally involves similar techniques used by the professional as well as by the individual. The individual typically utilizes tooth brushes and toothpaste to accomplish cleaning of the exterior surfaces of the teeth. The toothpaste itself may or may not contain abrasive materials. For cleaning between the teeth, dental floss is ordinarily utilized. Typically, dental floss comprises a string material such as cotton of an appropriate diameter to pass between the teeth and to aid in cleaning of the material between the teeth and at the gumline. The fiber material of dental floss is too soft to remove effectively tartar and other stain material from the surface of teeth.

It is the purpose of this invention to provide a flexible strip having scraping or scaling edges on the lateral surfaces thereof. The strip is inserted between the teeth and used in a manner similar to dental floss.

BRIEF SUMMARY OF THE INVENTION

In its preferred form, this invention comprises a thin flexible stainless steel strip which has been perforated in such a manner that peripheral raised edges, herein termed "scaling" or "scraping edges", are formed around the perforations on the lateral surfaces of the strip. Preferably, the scaling edge around each perforation is located on only one side of the strip so that the strip may be used to clean and burnish areas adjacent to composite and amalgam restorations safely.

The stainless steel selected for the strip is softer than tooth enamel. Tooth enamel hardness is approximately Brinell 350. The preferred Brinell hardness of the stainless steel strip is Brinell 260 or less. Other metals of appropriate hardness and flexibility may also be used although stainless steel is preferred since it lends itself most readily to autoclaving with other dental instruments. Thus, the strip can be reused until it dulls with repeated usage. Materials other than metal may be used for the strip such as plastic and the like.

BRIEF DESCRIPTION OF THE DRAWINGS

FIGS. 1 and 2 are edge and plan views, respectively, of a length of stainless steel strip, perforated according to the invention.

FIG. 3 is a cross-section taken along line 3—3 of FIG. 2 to illustrate a peripheral raised burr formed by punching a metalstrip so as to form a scaling or scraping edge.

FIG. 4 is a view similar to FIG. 2 showing a predetermined pattern of arrangement for the perforations in the strip.

FIG. 5 is a schematic showing of the strip in use between teeth.

DETAILED DESCRIPTION OF INVENTION

Referring to FIGS. 1 and 2, the preferred embodiment of the invention comprises, as shown, a length of stainless steel strip 10 such as type 301, 302 or 304 stainless, type 304 being most preferred. The metal of the strip is selected or treated, as by annealing, to be softer than ordinary tooth enamel. As already stated, tooth enamel hardness is approximately Brinell 350. Consequently, it has been determined that a Brinell hardness of 260 or less is satisfactory in this respect. Preferably, the hardness will not be less than Brinell 100. The strip, when completed according to the invention, can be sold in any convenient length, 10-foot lengths have been found to be acceptable. The thickness of the strip is selected so as to conveniently fit between teeth. Preferably, a thickness of 0.002 inches is used. However, this may vary. It is preferred, however, that the thickness remain below about 0.003 inches. A convenient height dimension h for the strip has been found to be 0.150 inches.

As can be seen from the Figures, the strip is perforated, perforations 12 may be arranged in various predetermined patterns. They may be aligned longitudinally on the strip as shown in FIG. 2. Another pattern is shown in FIG. 4 wherein the perforations overlap each other. Any shape may be selected for the perforation. The circular shape shown is preferred for ease in manufacture. Most preferably, perforations 12 will be, when circular in shape, about 0.040–0.050 inches in diameter and about 0.150 inches on center. Each perforation 12 includes a raised scaling or scraping edge 14, which extends peripherally around the associated perforation.

In forming raised peripheral scaling edges 14, the perforations 12 may be punched with tools designed to leave a small burr or to leave a large burr which may then be flattened to a suitable raised dimension such as 0.0015 inches. This dimension is not critical. However, it has been found that the overall thickness of the strip including the raised dimension of the scaling edge 14 is preferably about 0.0025 to 0.0035 inches. As previously pointed out, these dimensions are not critical and any dimensions are acceptable which will allow the strip to be inserted between the teeth and moved back and forth for scraping the dental plaque, calculus and stains in the interproximal contact areas between teeth. The burr or scaling edge 14 is shown in detail in FIG. 3.

In the preferred embodiment, as can be seen from the Figures, scaling edges 14 are all arranged on the same side of the strip. This makes the strip "safe-sided" so it can be used next to composites and other restorations to clean and burnish areas adjacent thereto safely. In certain instances, it may be desired to have scaling edges on both sides of the strip.

With this device, prophylaxis may be completed by inserting it between the teeth 15 as shown schematically in FIG. 5 and moving it back and forth in the same manner in which dental floss is used. It is self cleaning, carrying calculus out, and easily removing plague and stains from the hard-to-reach interproximal surfaces of teeth 16.

When formed of stainless steel, the strip does not tend to clog or fray. It is also reusable, autoclavable and cuts easily with scissors to any length desired for use. Three to four inches is all that is needed to work comfortably.

Ideal interproximal contact between teeth is zero. That is, the teeth should touch. The strip, when formed in thicknesses of 0.002 to 0.003 inches, about as thick as a sheet of paper, has been found to enter such contacts easily and comfortably without damage to teeth.

The strip has been found to be effective when used with or without prophylaxis paste.

Various changes may be made in the details of the invention. Thus, it is not intended to limit the invention to the specific embodiments described but rather to define the invention by the following claims.

I claim:

1. A prophylaxis strip for cleaning interproximal surfaces and contact areas between teeth, comprising: a length of thin, flexible, perforated strip, the material of which is softer than tooth enamel and hard enough to abrade plaque, calculus, stains and the like on teeth, the perforations of which are spacedly formed in the lateral surfaces of the strip, each perforation including a raised, peripheral scaling edge means on one of the lateral strip surfaces, the overall thickness of the strip being of a dimension which fits between the teeth.

2. A prophylaxis strip for cleaning interproximal surfaces and contact areas between teeth, comprising: a length of thin, flexible, perforated metal strip, the metal of which is softer than tooth enamel, the perforations of which are spacedly formed in the lateral surfaces of the strip, each perforation including a raised, peripheral, scaling edge on one of the lateral strip surfaces, the overall thickness of the strip being of a dimension which fits between the teeth.

3. The strip of claim 1 or 2 wherein the raised scaling edges are all carried on the same lateral surface of the strip, the other lateral surface being substantially smooth.

4. The strip of claim 2 wherein the overall thickness thereof is between about 0.0025 to 0.0035 inches.

5. The strip of claim 2 wherein the metal is stainless steel.

6. The strip of claim 2 wherein the metal has a Brinell hardness of about 260 or less.

7. The strip of claim 2 wherein the metal has a Brinell hardness of between about 100 and 260.

8. The strip of claim 2 wherein the raised dimension of the scaling edge is less than the thickness of the strip.

9. The strip of claim 2 wherein the thickness of the strip per se is about 0.002 inches.

10. The strip of claim 2 wherein the perforations are circular in shape and are about 0.040 to 0.050 inches in diameter.

11. The strip of claim 2 wherein the scaling edges are burrs resulting from a punching operation used to form the perforations in the strip.

12. The strip of claim 2 wherein the thickness of the strip per se is less than about 0.003 inches.

13. The strip of claim 2 wherein the raised dimension of the scaling edges is less than about 0.0015 inches.

14. The strip of claim 2 wherein the metal is type 304 stainless steel.

15. The strip of claim 2 wherein the perforations are arranged in a predetermined pattern.

* * * * *